(12) United States Patent
Hamman et al.

(10) Patent No.: US 8,814,978 B2
(45) Date of Patent: *Aug. 26, 2014

(54) METHOD AND APPARATUS FOR FORMING POROUS METAL IMPLANTS

(71) Applicant: Biomet Manufacturing, LLC, Warsaw, IN (US)

(72) Inventors: Ned M. Hamman, Leesburg, IN (US); James B. Fleming, Warsaw, IN (US); Isaac Janson, South Bend, IN (US); Mukesh Kumar, Warsaw, IN (US); Jason Meridew, Syracuse, IN (US); Elizabeth A. Schlueter, Gainseville, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/738,616

(22) Filed: Jan. 10, 2013

(65) Prior Publication Data

US 2013/0118377 A1    May 16, 2013

Related U.S. Application Data

(60) Division of application No. 13/021,987, filed on Feb. 7, 2011, now Pat. No. 8,361,380, which is a continuation of application No. 12/558,300, filed on Sep. 11, 2009, now Pat. No. 7,883,661, which is a continuation of application No. 11/357,929, filed on Feb. 17, 2006, now Pat. No. 7,635,447.

(51) Int. Cl.
B22F 1/00 (2006.01)

(52) U.S. Cl.
USPC ........................................ 75/252; 252/182.33

(58) Field of Classification Search
USPC .......................................................... 75/252
See application file for complete search history.

(56) References Cited

U.S. PATENT DOCUMENTS

| | | |
|---|---|---|
| 3,855,638 A | 12/1974 | Pilliar |
| 4,156,943 A | 6/1979 | Collier |
| 4,206,271 A | 6/1980 | Norling et al. |
| 4,309,488 A | 1/1982 | Heide et al. |
| 4,412,643 A | 11/1983 | Sato et al. |
| 4,550,448 A | 11/1985 | Kenna |
| 4,612,160 A | 9/1986 | Donlevy et al. |
| 4,644,942 A | 2/1987 | Sump |
| 4,846,393 A | 7/1989 | Devillard |
| 4,957,819 A | 9/1990 | Kawahara et al. |
| 5,047,182 A | 9/1991 | Sundback et al. |
| 5,080,672 A | 1/1992 | Bellis |
| 5,096,518 A | 3/1992 | Fujikawa et al. |
| 5,104,410 A | 4/1992 | Chowdhary |
| 5,126,103 A | 6/1992 | Ishizaki et al. |
| 5,201,766 A | 4/1993 | Georgette |
| 5,282,861 A | 2/1994 | Kaplan |
| 5,348,788 A | 9/1994 | White |
| 5,504,300 A | 4/1996 | Devanathan et al. |
| 5,507,824 A | 4/1996 | Lennox |
| 5,535,810 A | 7/1996 | Compton et al. |
| 5,688,453 A | 11/1997 | England et al. |
| 5,702,458 A | 12/1997 | Burstein et al. |
| 5,734,959 A | 3/1998 | Krebs et al. |
| 5,926,685 A | 7/1999 | Krebs et al. |
| 6,022,509 A | 2/2000 | Matthews et al. |
| 6,066,176 A | 5/2000 | Oshida |
| 6,132,674 A | 10/2000 | Compton et al. |
| 6,458,161 B1 | 10/2002 | Gibbs et al. |
| 6,495,448 B1 | 12/2002 | Lee |
| 6,527,809 B1 | 3/2003 | Doursounian et al. |
| 6,544,472 B1 | 4/2003 | Compton et al. |
| 6,605,648 B1 | 8/2003 | Johnson et al. |
| 6,660,224 B2 | 12/2003 | Lefebvre et al. |
| 6,913,623 B1 | 7/2005 | Zhu |
| 6,945,448 B2 | 9/2005 | Medlin et al. |
| 7,147,819 B2 | 12/2006 | Bram et al. |
| 7,291,177 B2 | 11/2007 | Gibbs |
| 7,351,371 B2 | 4/2008 | Nelles et al. |
| 7,597,715 B2 | 10/2009 | Brown et al. |
| 8,383,088 B2 | 10/2009 | Gupta |
| 7,635,447 B2 | 12/2009 | Hamman et al. |
| 7,713,306 B2 | 5/2010 | Gibbs |
| 7,918,382 B2 | 4/2011 | Charlebois et al. |
| 2002/0062154 A1 | 5/2002 | Ayers |
| 2003/0083741 A1 | 5/2003 | Woo et al. |
| 2003/0153981 A1 | 8/2003 | Wang et al. |

(Continued)

FOREIGN PATENT DOCUMENTS

| | | |
|---|---|---|
| DE | 3130732 | 5/1983 |
| DE | 19726961 | 11/1998 |

(Continued)

OTHER PUBLICATIONS

Bram et al. "High-Porosity Titanium, Stainless Steel, and Superalloy Parts" Advanced Engineering Materials, vol. 2, No. 4 (2000) pp. 196-199.

(Continued)

Primary Examiner — George Wyszomierski
Assistant Examiner — Ngoclan T Mai
(74) Attorney, Agent, or Firm — Harness, Dickey

(57) ABSTRACT

A method for providing a porous metal implant. A mixture of a biocompatible metal, a spacing agent, and a binder is provided. The mixture is formed into a shaped the spacing agent is removed to form a plurality of pores in the implant. A shaped porous metal implant is also provided.

12 Claims, 5 Drawing Sheets

(56) References Cited

U.S. PATENT DOCUMENTS

| | | |
|---|---|---|
| 2003/0171820 A1 | 9/2003 | Wilshaw et al. |
| 2003/0200837 A1 | 10/2003 | Matsuura et al. |
| 2003/0220696 A1 | 11/2003 | Levine et al. |
| 2003/0232124 A1 | 12/2003 | Medlin et al. |
| 2004/0064192 A1 | 4/2004 | Bubb |
| 2004/0072010 A1 | 4/2004 | Date et al. |
| 2004/0109853 A1 | 6/2004 | McDaniel |
| 2004/0137218 A1 | 7/2004 | Liu et al. |
| 2005/0031704 A1 | 2/2005 | Ahn |
| 2005/0048193 A1 | 3/2005 | Li et al. |
| 2005/0100470 A1 | 5/2005 | Lefebvre et al. |
| 2005/0145364 A1 | 7/2005 | Nakajima |
| 2005/0234559 A1 | 10/2005 | Fernandez et al. |
| 2005/0242162 A1 | 11/2005 | Medlin et al. |
| 2006/0002810 A1 | 1/2006 | Grohowski, Jr. |
| 2006/0018942 A1 | 1/2006 | Rowe et al. |
| 2006/0241776 A1 | 10/2006 | Brown et al. |
| 2006/0241781 A1 | 10/2006 | Brown et al. |
| 2007/0129809 A1 | 6/2007 | Meridew et al. |
| 2007/0150068 A1 | 6/2007 | Dong et al. |
| 2007/0173948 A1 | 7/2007 | Meridew et al. |
| 2007/0243312 A1 | 10/2007 | Bulko |
| 2007/0250175 A1 | 10/2007 | Meridew et al. |
| 2007/0264152 A1 | 11/2007 | Zhao |
| 2008/0027556 A1 | 1/2008 | Metzger |
| 2008/0147187 A1 | 6/2008 | Bollinger et al. |
| 2008/0195222 A1 | 8/2008 | Rauguth et al. |
| 2008/0199343 A1 | 8/2008 | Rust et al. |
| 2009/0084491 A1 | 4/2009 | Uthgenannt et al. |
| 2009/0098310 A1 | 4/2009 | Hippensteel et al. |
| 2010/0004754 A1 | 1/2010 | Brown et al. |
| 2010/0074789 A1 | 3/2010 | Heuer et al. |

FOREIGN PATENT DOCUMENTS

| | | |
|---|---|---|
| EP | 1421918 | 5/2004 |
| JP | 3837502 | 8/2006 |
| WO | WO 2004/080340 | 9/2004 |
| WO | WO 2006/007861 | 1/2006 |

OTHER PUBLICATIONS

Laptev, A. et al. "Study of Production Route for Titanium Parts Combining Very High Porosity and Complex Shape" Powder Metallurgy, vol. 47, No. 1 (2004) pp. 85-92.

Li, J. et al. "A Novel Porous Ti6Al4V: Characterization and Cell Attachment" Journal of Biomedical Materials Research, vol. 73a, No. 2, pp. 223-233 (May 2005).

Oliveira et al. "Porous Structure Characterization in Titanium Coating for Surgical Implants" Materials Research, vol. 5, No. 3 (2002) pp. 269-273.

Wen, C.E. et al. "Novel Titanium Foam for Bone Tissue Engineering" J. Mater. Res., vol. 17, No. 10 (2002) pp. 2633-2639.

Wen, C.E. et al. "Processing and Mechanical Properties of Autogenous Titanium Implant Materials" Journal of Materials Science: Materials in Medicine 13 (2002) pp. 397-401.

Wen, C.E. et al. "Processing of Biocompatible Porous Ti and Mg" Scripta Materialia 45 (2001) pp. 1147-1153.

Wheeler, K.R. et al. "Porous Metals as a Hard Tissue Substitute. Part II: Porous Metal Properties" Biomat., Med. Dev., Art. Org., 1(2), (1973) pp. 337-348.

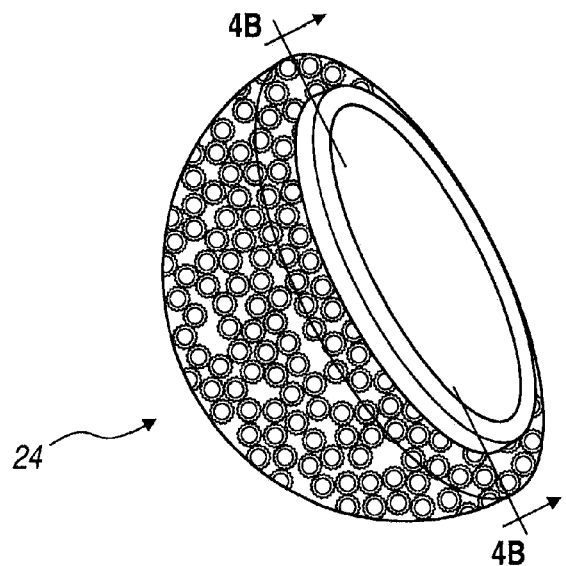
FIG. 5A
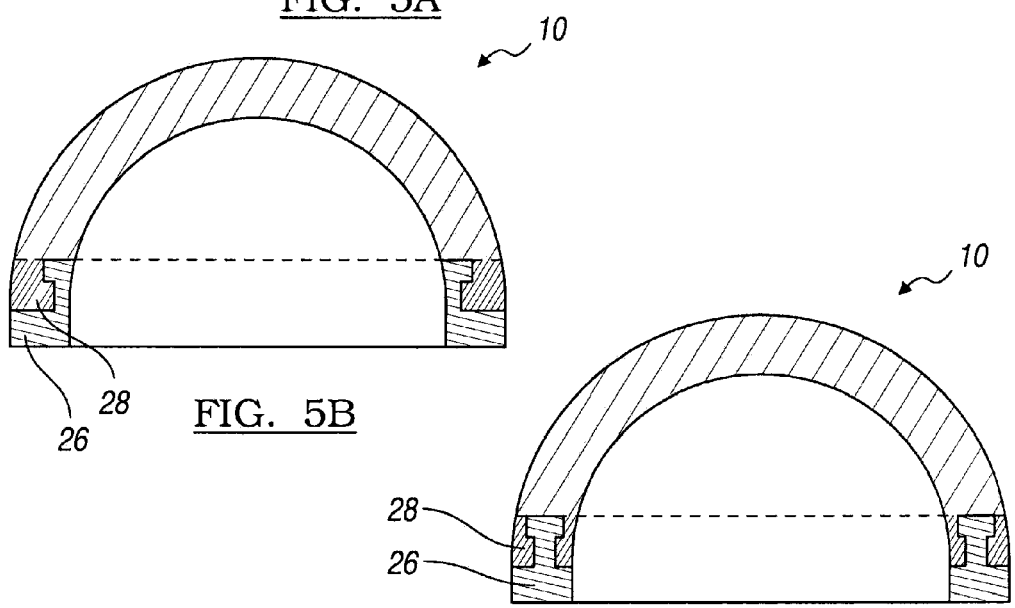
FIG. 5B
FIG. 5C

METHOD AND APPARATUS FOR FORMING POROUS METAL IMPLANTS

CROSS-REFERENCE TO RELATED APPLICATIONS

This application is a divisional of U.S. patent application Ser. No. 13/021,987, filed Feb. 7, 2011 (issued as U.S. Pat. No. 8,361,380 on Jan. 29, 2013), which is a continuation of U.S. patent application Ser. No. 12/558,300, filed Sep. 11, 2009 which is a continuation of U.S. patent application Ser. No. 11/357,929, filed Feb. 17, 2006 (issued as U.S. Pat. No. 7,635,447 on Dec. 22, 2009), the disclosures of which are incorporated herein by reference. The present application is related to U.S. patent application Ser. No. 11/357,868, filed Feb. 17, 2006 (issued as U.S. Pat. No. 7,597,715 on Oct. 6, 2009) entitled "Method and Apparatus for Use of Porous Implants", the disclosure of which is incorporated by reference. U.S. Pat. No. 7,597,715 is commonly assigned to Biomet Manufacturing, LLC of Warsaw, Ind.

FIELD

The present teachings relate to porous metal implants and methods of manufacture.

BACKGROUND

Porous metal implants are used to promote ingrowth of surrounding bony tissue and soft tissues into the implant. When the porosity, integrity and continuity of the metals are sufficient, porous implants serve as a scaffold for tissue ingrowth to provide the desired load-bearing strength to the implant site.

The porous implants can be formed by removing pieces from a metal substrate, such as by etching a solid piece of metal. The implants can also be formed by using small metal particles such as powders. Where metal powders are used, multi-step heat and pressure application steps can compromise the desired integrity and load-bearing strength of the implant due to shifts in the structure during initial molding and when transferring the implant between the various furnaces, pressure chambers, machining apparatus, etc. Furthermore, temperatures and pressures must accommodate the removal of foaming agents or spacing agents without further compromising the implant. These multiple considerations in forming the implant limit the formation of complex shapes from the starting materials because switching between the various pressing, heating, shaping, and other processing steps can cause the implant to become misshapen. In other systems using metal powders, a binding or interface layer must be used in order to attach the porous structure to a substrate. Many of these methods use different metals to form the substrate and the porous layer, leading to corrosion and a reduction in the life span of the implant.

It may be desirable to provide a porous metal implant which has one or more of these properties: a desirable porosity, is shaped and processed easily, readily forms three-dimensional complex shapes, maintains its intended shape throughout the various processing steps, promotes soft and hard tissue ingrowth, and is suitable for load-bearing applications.

SUMMARY

The present teachings provide methods for preparing a porous metal implant comprising: preparing a mixture of a biocompatible metal powder; a spacing agent; and a non-polar liquid binder, where the spacing agent is substantially insoluble in the non-polar liquid binder. The mixture is formed into a shape and the non-polar liquid binder and the spacing agent are removed from the mixture to form a plurality of pores within the metal implant.

The biocompatible metal powder can be selected from titanium, titanium alloys, cobalt, cobalt alloys, chromium, chromium alloys, tantalum, tantalum alloys, and stainless steel. The biocompatible metal powder can have a particle size of from about 5 micrometers to about 1500 micrometers. The spacing agent can be selected from hydrogen peroxide, urea, ammonium bicarbonate, ammonium carbonate, ammonium carbamate, calcium hydrogen phosphate, naphthalene, and mixtures thereof. The spacing agent can have a particle size of from about 1 micrometer to about 1500 micrometers. The non-polar liquid binder and the spacing agent can form a suspension. The non-polar liquid binder can comprise d-limonene (commercially available from Florida Chemical Company, Inc., Winter Haven, Fla., United States). The binder and the spacing agent can be cohesive during formation of the mixture and removal of the spacing agent. The mixture can be homogenous. The mixture can be formed into a shape suitable for application to an augment site.

Forming the mixture into a shape can be achieved with pressing techniques such as uniaxial pressing, isostatic pressing, and split die techniques and can be conducted at or below about room temperature. The pressing technique can be conducted at a pressure of from about 100 megapascals to about 500 megapascals. Generally, a suitable pressure is at about or above 150 megapascals or above 170 megapascals. Removing the spacing agent can include subliming the mixture at a temperature at which the metal does not react with the spacing agent. The mixture can be sintered under vacuum pressure after removing the spacing agent. The formed shape can be further shaped, machined, attached to a substrate, or welded to a substrate.

The porosity of the implant can be varied by using metal powder(s) or spacing agent(s) of at least two different sizes. The porosity can be continuous or it can be a gradient. The gradient can include porosity changes of from about 1% to about 80%. The implant can also be coated with agents such as resorbable ceramics, resorbable polymers, antibiotics, demineralized bone matrix, blood products, platelet concentrate, allograft, xenograft, autologous, and allogeneic differentiated or stem cells, peptides, nutrients, vitamins, growth factors, and combinations thereof.

The present teachings also provide moldable compositions for providing a porous metal implant. The compositions include a biocompatible metal powder; a spacing agent; and a non-polar liquid binder, where the spacing agent is substantially insoluble in the non-polar liquid binder. The biocompatible metal powder can independently comprise Ti-6Al-4V, the spacing agent can comprise ammonium bicarbonate, and the non-polar liquid binder can comprise d-limonene. The materials can be selected such that the sublimation temperature of the spacing agent and the sublimation temperature of the non-polar liquid binder differ by less than about 200° C. The moldable composition can include a securing element.

The present teachings also provide methods of securing a moldable composition, comprising: placing a securing element about at least a portion of the mixture; molding the mixture into a formed shape while the mixture is in the securing element; subliming the spacing agent and non-polar liquid binder from the formed shape; removing the securing element; and sintering the formed shape. The securing element can be a flexible material and can be secured about at least a portion of the mixture using a vacuum seal. The foil can have a thickness of about 1 millimeter. The securing element can enhance the cohesiveness of the formed shape for at least three days.

The present teachings also provide methods for preparing a porous metal implant comprising: preparing a mixture comprising a biocompatible metal powder, a spacing agent, and a non-polar liquid binder, where the spacing agent is substantially insoluble in the non-polar liquid binder; forming the mixture into a shape; and thermal cycling the mixture within a single heating unit to remove the spacing agent and the non-polar liquid binder and sinter the metal powder to form a plurality of pores within the metal implant. The mixture can be continuously maintained in the heating unit until the metal powder combines to form the metal implant. The thermal cycling can include at least one sintering and at least one quenching.

Further areas of applicability of the present teachings will become apparent from the detailed description provided hereinafter. It should be understood that the detailed description and specific examples, are intended for purposes of illustration only and are not intended to limit the scope of the teachings.

BRIEF DESCRIPTION OF THE DRAWINGS

FIG. 5A through 5C depict porous metal implants used in conjunction with an acetabular cup prosthesis according to various embodiments;

DETAILED DESCRIPTION

The following description is merely exemplary in nature and is in no way intended to limit the teachings, their application, or uses. Although various embodiments may be described in conjunction with a porous metal implant for use with a knee or hip prosthetic device, it is understood that the implants and methods of the teachings can be of any appropriate substrate or shape and can be used with any appropriate procedure and not solely those illustrated.

Figure 1:
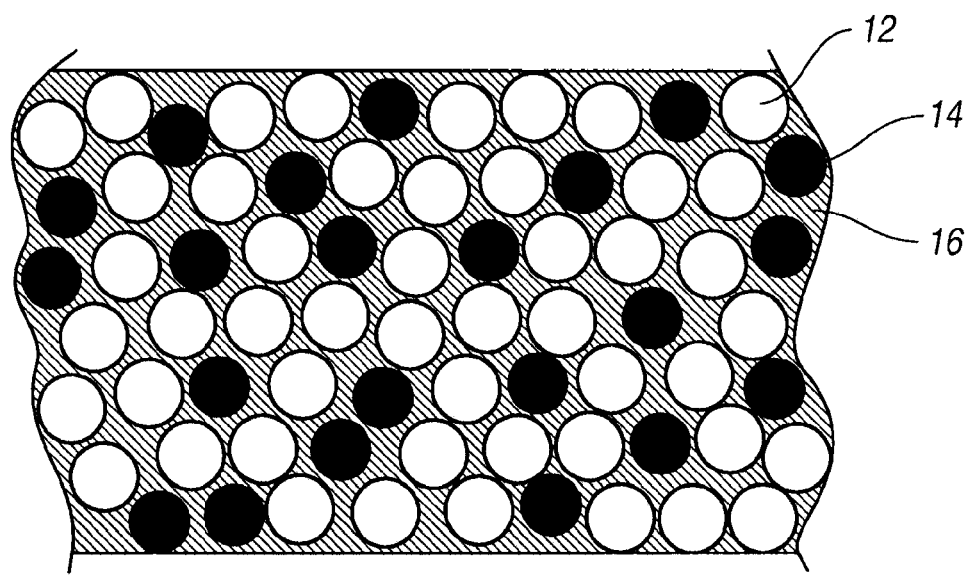
FIG. 1 depicts a mixture used to prepare a porous metal implant according to various embodiments.
Figure 2:
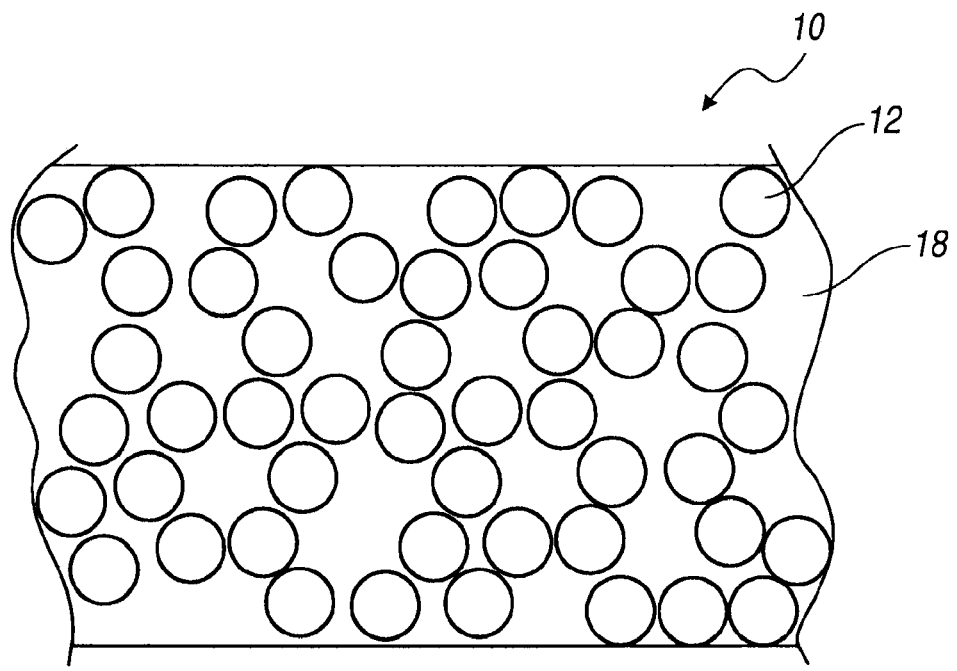
FIG. 2 depicts a porous metal implant according to various embodiments.

Referring to FIGS. 1 and 2, a porous metal implant 10 can be formed from a mixture of a metal powder 12, a spacing agent 14, and a non-polar liquid binder 16. The porous metal implant 10 is formed by heating the mixture to a temperature sufficient to remove the spacing agent 14 and non-polar liquid binder 16 thereby leaving a plurality of pores 18 between the interconnected metal powder 12 particles.

The metal powder 12 can be any metal or alloy that is suitable for use as an implant and provides the desired strength, load bearing capabilities, and ability to become porous. Suitable exemplary metals include titanium, cobalt, chromium, or tantalum, alloys thereof, stainless steel, and combinations thereof. The metal powder 12 particles can have a diameter of from about 5 micrometers to about 1500 micrometers. In various embodiments, the metal powder 12 can be of at least two different particle sizes.

The spacing agent 14 provides the pores 18 of the porous metal implant 10. The spacing agent 14 can be removable from the mixture and it may be desirable if the spacing agent 14 does not leave residue in the porous metal implant 10. It may be further desirable that the spacing agent 14 expands or contracts to supplement the formation of pores 18 of a desired size within the porous metal implant 10. The spacing agent 14 can be selected from the group consisting of hydrogen peroxide, urea, ammonium bicarbonate, ammonium carbonate, ammonium carbamate, calcium hydrogen phosphate, naphthalene, and mixtures thereof, or can be any other suitable subliming and space forming material. Generally, the spacing agent 14 has a melting point, boiling point, sublimation temperature, etc. of about less than 250° C. The spacing agent 14 provides the macroporosity and microporosity of the biocompatible metal powder 12 before and during the thermal cycling processes, described later herein, because after the spacing agent 14 decomposes and metallurgical bonds form between the metal powder 12 particles, pores 18 or gaps remain where the spacing agent 14 was located.

The non-polar liquid binder 16 is used to improve the cohesiveness of the mixture because the non-polar liquid binder 16 keeps all mixture components in close proximity and does not dissolve the spacing agent 14. The non-polar liquid binder 16 can be a volatile compound with a boiling point sufficiently close to the sublimation or decomposition point of the spacing agent 14. In various embodiments, that temperature difference is less than about 200° C. In still other embodiments, that difference is less than about 100° C. The close range of the sublimation temperature of the spacing agent 14 and the boiling point of the non-polar liquid binder 16, allows for a single step removal of the spacing agent 14 and the non-polar liquid binder 16.

The non-polar liquid binder 16 can be a botanical organic compound. An example of such a binder is limonene (4-isopropenyl-1-methylcyclohexene), including any stereoisomers thereof, such as d-limonene, l-limonene, and mixtures thereof. In various embodiments, d-limonene can be used. The d-limonene can be derived from citrus fruits (orange, lemon, lime, tangerine, etc.), from other plant materials such as those in the genus *Pinus* (from pine tree needles and branches), *Peucedanum* (from dill plants), and other plants. In embodiments where the non-polar binder 16 is derived from a citrus fruit, it is preferred that the major component is d-limonene and the balance consists of other terpene hydrocarbons and oxygenated compounds such as octanal, myrcene, alpha-pinene, and linalool. The d-limonene can be synthesized in a laboratory (non-fruit derived) or processed from the plant to be of food or technical grades. Other suitable non-polar liquid binders 16 can include high concentrations of terpenes, relative to other components in the material, such as those derived from cedar wood, *Copaiba Balsam*, ginger, hemp, hops, bergamot, dog fennel, turpentine, pinene, and sylvestrene, for example. In various embodiments, a mixed terpene solution can be used, the mixture consisting of various concentrations of terpenes, sesquiterpenes, and polyterpenes. It is understood that the non-polar liquid binder 16 is not limited to botanicals, but also includes any non-polar liquid having the desired volatility and/or compatibility with the metal powder 12 and the spacing agent 14, etc., for example mineral oil.

The mixture of non-polar liquid binder 16, spacing agent 14, and metal powder 12 can be made homogenous by mixing. In various embodiments, the ratio of metal powder 12 to spacing agent 14 can be about 1:1 up to about 10:1. The non-polar liquid binder 16 can be in a ratio of from about 1 part binder (in milliliters) to about 10 parts of solid (spacing agent 14 and biocompatible metal powder 12, in grams) up to about 1 part binder 16 to about 30 parts of solid.

Altering the ratios of the mixture components and/or the sizes of the components can provide an implant having a higher or lower porosity, enhanced load-bearing abilities, and can help to tailor the porous metal implant 10 for a particular region of the body. Utilizing a ratio of metal powder 12 to spacing agent 14 of 8:1 will provide an dense implant 10 having very fine pores. In another example, in a mixture having a 3:1 metal powder 12 to spacing agent 14 ratio, if the spacing agent 14 has a diameter of at least about 25 micrometers and the metal powder 12 has a diameter of about 10 micrometers, large pores result. If the metal powder 12 and spacing agent 14 diameter sizes were reversed, smaller pores would result.

The mixture can also include metal powders 12 of different particulate sizes. By including metal powder 12 particulates of at least two different sizes, a porosity gradient can be achieved. The porosity gradient can be such that the porosity of the implant 10 increases or decreases by up to about 80% across the body of the implant 10. The porosity gradient can be continuous and scale up (or down) to a desired amount, or the porosity gradient can include differing porosity regions (e.g., 80% porosity region transitions to a 40% porosity region which transitions to a 75% porosity region). The transitions between the regions can be continuous in the porous metal implant 10. To provide the different porosities, a mixture corresponding to a particular porosity is stacked on top of or adjacent to a mixture having a different porosity.

Figure 3A:
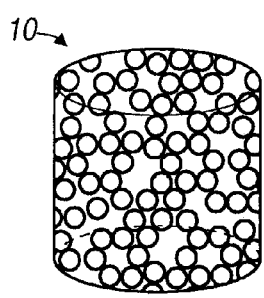
FIG. 3A through 3H depict various shaped porous metal implants according to various embodiments.
Figure 3E:
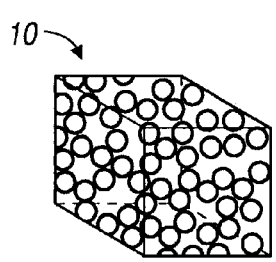
Figure 3H:
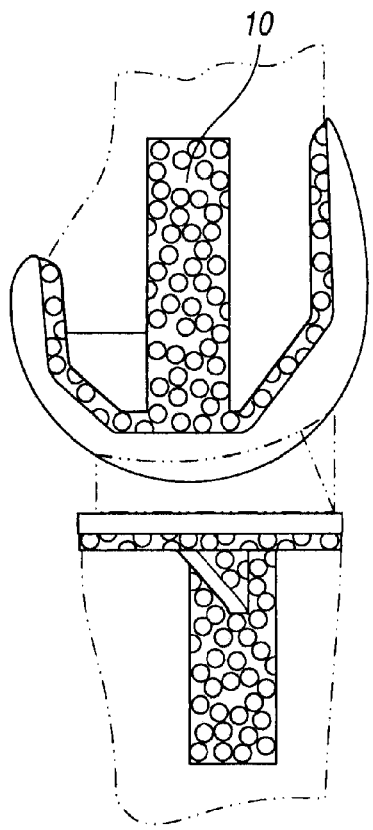
Figure 3B:
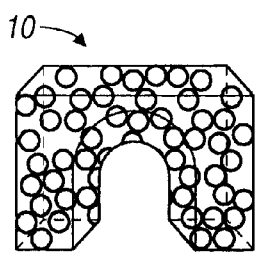
Figure 3F:
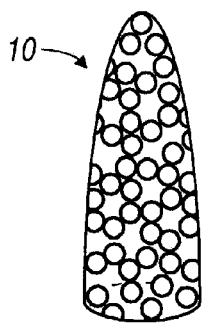
Figure 3C:
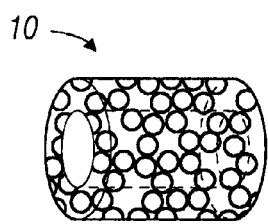
Figure 3D:
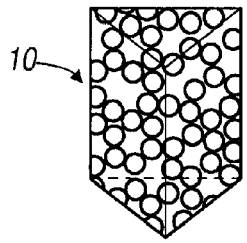
Figure 3G:
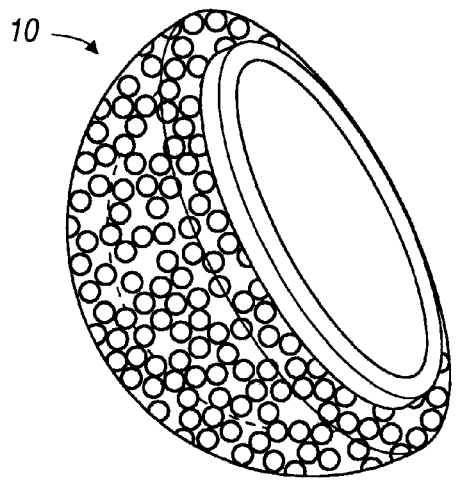

The mixture can be formed into a regular or geometric shape. As depicted in FIGS. 3A-3F, the shaped mixture can be used to form implants that include solid body cylinders, blocks, discs, cones and also include hollow or recessed regions as depicted in FIGS. 3B and 3C. The mixture can also be a free form shape such as a shape corresponding to an augment, site in a recipient to provide a prosthetic specifically tailored to a recipient. The combination of the metal powder 12, spacing agent 14, and non-polar liquid binder 16 allows for shaping the mixture prior to any heat treatments described later herein. Shaping the mixture prior to sintering simplifies the process of forming the porous metal implant 10 by eliminating the need to transfer the mixture from between a heat source for subliming the spacing agent 14, a different heat source to remove the non-polar liquid binder 16, and any machines.

Figure 4A:
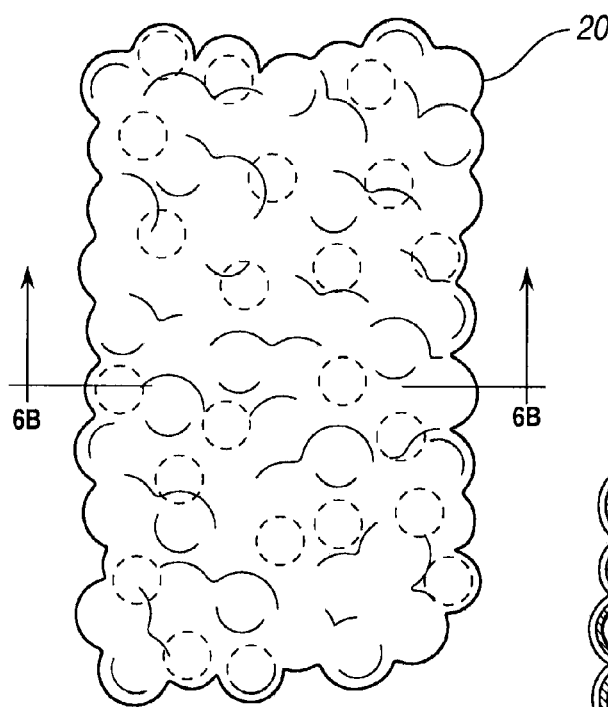
FIG. 4A depicts a secured preparation to form a porous metal implant according to various embodiments.
Figure 4B:
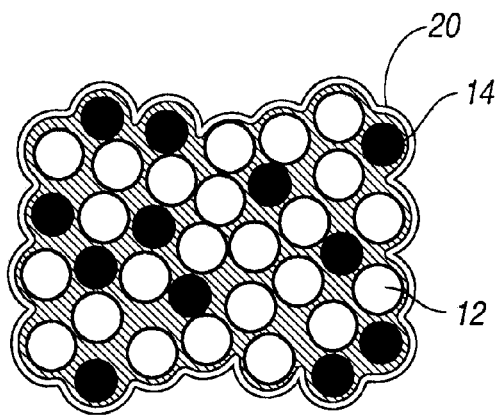
FIG. 4B depicts an interior view of the secured preparation depicted in FIG. 4A.

Referring to FIGS. 4A and 4B, to facilitate forming the porous metal implant 10 into a shape, the mixture can be fixed into place with a securing element 20. The securing element 20 can contact at least a region of the mixture for the porous metal implant 10. The securing element 20 can be made of a flexible material that is substantially non-reactive with the metal powder 12, the spacing agent 14, and/or the non-polar liquid binder 16. The securing element 20 can be a metal foil, such as aluminum foil for example. The securing element 20 can also be a rubber material or a silicone polymer. The thickness of the securing element 20 can be greater than about 1 millimeter, but it can be scaled up or down depending on the size of the porous metal implant 10 and the ratio of the non-polar liquid binder 16 to the metal powder 12 and the spacing agent 14. For example, if the mixture had a critical volume of the non-polar liquid binder 16, it may be desirable to employ a thicker foil securing element 20 to prevent any unintentional release of the non-polar binder 16 from the wrapped package. The securing element 20 can be a band or piece of foil that can be attached to a portion of the mixture, folded upon itself, or form a pouch to envelop the mixture. The packet of the mixture wrapped in the securing element 20 can be formed into a shape, such as those in FIGS. 3A-3H without damaging the mixture or disrupting a porosity gradient, if any, in the material.

The securing element 20 increases the time the mixture can be stored prior to thermal cycling. The securing element 20 increases the cohesiveness of the mixture of the metal powder 12, the spacing agent 14, and the binder 16 to reduce unintentional separation of disruption of the material, even, for example, when the mixture is arranged to provide a porosity gradient. The cohesiveness refers to the ability of the metal powder 12, the spacing agent 14, and the binder 16 to be held together as a solid mass of the respective discrete materials. For example, the mixture can be held for several hours, from 1 to 7 days, from about 3 to about 12 weeks, for a period of several years, or longer. In embodiments where the non-polar liquid binder 16 is d-limonene, the mixture is particularly shelf-stable. Shelf-stability is particularly advantageous when preparation of the mixture needs to be completed at an earlier time than the sintering of the mixture or when resources are limited as to the amount of heating units, such as ovens, furnaces, etc. available and the number/variety of porous metal implants 10 that need to be created.

Figure 6:
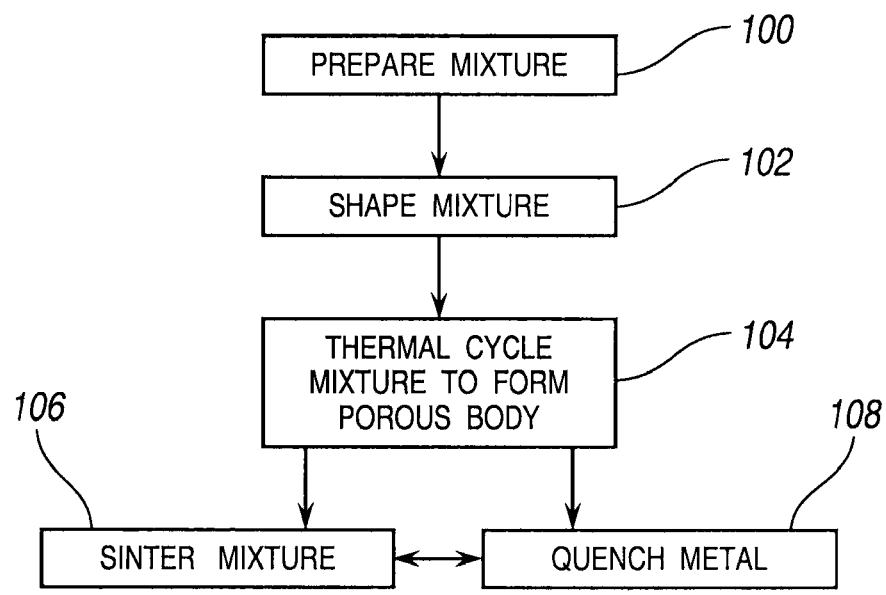
FIG. 6 is a diagram of a method of forming a porous metal implant.

FIG. 6 generally details the methods of forming the porous metal implant 10. Forming the porous metal implant 10 generally includes preparing the mixture 100, shaping the mixture 102, and thermal cycling the mixture to form the porous body 104. Preparing the mixture 100 is detailed above herein. Shaping the mixture can include pressing the mixture in a suitable device including an isostatic press, uniaxial press, or a split die to form a compact. The mixture can be placed in a rubber mold or any other suitable mold to maintain the shape during the press. In various embodiments, the press is conducted at or below about 200° C. or at or below about room temperature. For example, a cold isostatic press can be used where the temperature is less than about 200° C. The metal-binder-spacing agent mixture is placed in a cold isostatic press bag and pressure is applied. An alternate forming includes shaping the blocks formed from the cold isostatic or other pressing into specific shapes. The pressure used in from about 345 kilopascals to about 420 kilopascals. The formed shapes or blocks can be machined into particular shapes (e.g., acetabular cup). The pressed compacts can also be stored in airtight sealed containers or foil bags.

The thermal cycling 104 includes removing the spacing agent 14 and the non-polar liquid binder 16 and sintering the mixture to create metallic interparticle bonds and provide the physical and mechanical properties of the porous metal implant 10. The thermal cycling 104 can include at least one sintering 106 and at least one quenching 108. Sintering conditions (temperature, time, and atmosphere) must be such that the metallic interparticle bonds are created while extensive densification is avoided. The sintering can be performed in a controlled atmosphere, such as a vacuum for example, to prevent formation of oxides on the metal surface. Thermal cycling can be a single-oven or furnace process and require no manipulation of the mixture between the stages of forming the mixture and removing formed porous metal implant 10. It is also understood that the thermal cycling of the materials described herein can be performed in multiple ovens.

In an exemplary cycling, the compact can be initially heated at from about 50° C. to about 250° C. to remove the non-polar liquid binder 16 and the spacing agent 14. The exact temperature can be selected depending on the combination of the non-polar liquid binder 16 and the spacing agent 14, vacuum conditions, etc. It is desirable to remove the spacing agent 14 at a temperature at which the metal 12 does not react with the spacing agent 14. In various embodiments, that temperature can be at from about 25° C. to about 500° C. In various other embodiments, that temperature can be a temperature less than the melting point of the metal powder 12. For example, in an embodiment where the non-polar liquid binder 16 comprises d-limonene having a boiling point of 175° C. and an ammonium bicarbonate spacing agent having a boiling temperature of 108° C. and begins to decompose carbon dioxide. A suitable initial cycling temperature can be at about at least 60° C. or higher, but preferably under the sintering temperature of the selected metal powder 12. It may be desirable for the initial cycle temperature to be at about or above the boiling point or the sublimation point or decomposition of the component having the highest temperature value. In the above example, it may be desirable to use an initial cycling temperature of about 175° C.

A first sintering of the compact is conducted to transform the compact (substantially free from metallurgical bonds between the metal powder 12 particles) to the implant 10 having the metallurgical bonds. The temperature can be increased in the chamber (2° C., 5° C., 10° C., 20° C., 50° C., for example) at time intervals (5 seconds up to 15 minutes). Once the desired temperature or "hold temperature" is reached, the mixture is maintained at the hold temperature from about 1 hour to about 10 hours or from about 2 hours to about 6 hours to create the metallurgical bonds between the metal powder 12 particles. The use of temperature intervals allows for elimination of separate steps or separate ovens used to remove the spacing agent 14 and the non-polar liquid binder 16.

The porous metal implant 10 is quenched or rapidly cooled to generate a phase of hardened metal known as the martensite phase. Quenching can be achieved by direct quenching, fog quenching, hot quenching, interrupted quenching, selective quenching, slack quenching, spray quenching, and/or time quenching. Quenching can be performed in the sintering oven without moving the implant. For example, with fog quenching, a fog could be distributed through the sintering oven to quench the metal and the fog could be subsequently vacuumed out. Once the sintering oven was completely purged of the fog, an inert gas could be reintroduced into the oven and the thermal cycling would continue. The porous metal implant 10 can be quenched at or below room temperature or the porous metal implant 10 can be quenched to a warmer temperature (over about 40° C.). For example, the porous metal implant 10 can be quenched to a temperature closer to the starting temperature of the subsequent sintering or heating. In such embodiments, if the first sintering hold temperature was over 1000° C., the quenching can reduce the temperature of the porous metal implant 10 to about 400° C.

A second sintering can also be employed. The second sintering can be conducted under similar conditions to the first sintering or the hold temperature can be reduced as compared with the first sintering. For example, where the first hold temperature was over 1000° C., the second hold temperature can be from about 500° C. to about 900° C. The second hold time can be of the same duration or a different duration than the first hold time. In various embodiments, the hold time can be from about 1 hour to about 10 hours or from about 2 hours to about 6 hours. Quenching as detailed above can also be repeated. Furthermore, additional sintering can be performed.

After completion of sintering, a final thermal treatment can include heating the porous implant 10 at a temperature below the sintering temperature of the metal powder 12 or at a temperature that is a fraction of the first sintering temperature. In various embodiments, it may be desirable to employ a fraction gradient temperature reduction. For example, a first sintering can be up to a temperature of about 1200° C., a second sintering can be up to about 800° C., and the final thermal treatment can be up to about 400° C. Each successive heating can be reduced by a predetermined number of degrees, for example about 300° C. to about 400° C. Between each heating, quenching can be employed to increase the hardness and longevity of the porous metal implant 10, while preventing the crumbling and misshapen attributes caused by moving the materials between the various ovens or machines, for example. In various embodiments, it may be desirable to quench the porous implant to about room temperature during the final thermal cycling.

The thermal cycling can be conducted in a vacuum or under reduced pressure of inert gas. It may be desirable to conduct the sintering in an inert atmosphere (in argon gas, for example). The vacuum and/or the inert atmosphere will prevent solid solution hardening of the surface of the porous implant 10 as a result of inward diffusion of oxygen and/or nitrogen into the metal.

The porous implant 10 can be further shaped and machined to adjust the tolerances of the material and can be used to add features such as grooves, indentations, ridges, channels, etc. The machining can also be used to form complex shapes such as those depicted in FIGS. 3G and 3H.

The porous metal implant 10 can be attached to a metal substrate 22 by any suitable means, such as welding, sintering, using a laser, etc. In various embodiments, the metal substrate is the same metal as the metal powder 12. The metal substrate can be a prosthetic device, such as an acetabular cup, depicted in FIG. 3G, or to the condoyle surfaces, depicted in FIG. 3H. The temperature and pressure conditions used to attach the metal substrate to the porous body can be such that diffusion and metallurgical bonding between the substrate surface areas and the adjacent porous metal surfaces will be achieved. For example, in an embodiment where the porous metal segment and metal substrate are heated to 1000° C., the pressure applied must be such that the resultant implant 10 has structural integrity for implanting into a recipient without significant defects.

Figure 7:
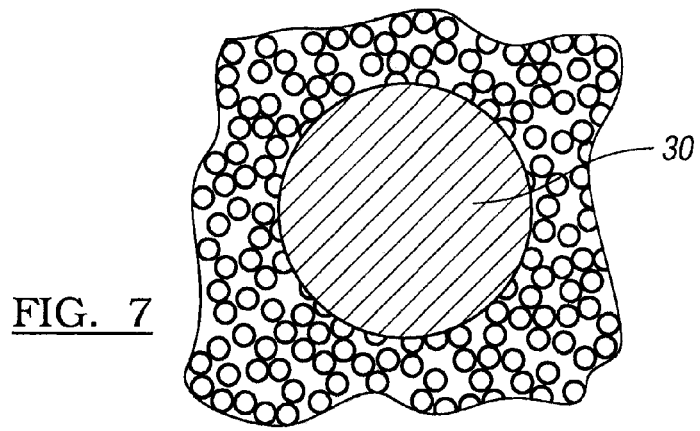
FIG. 7 depicts a porous metal implant attached to a solid core according to various embodiments.

The metal substrate 22 can be prepared prior to attaching the porous body. The metal substrate 22 can be acid etched, subjected to an acid bath, grit blasted, or ultrasonically cleaned for example. Other preparations include adding channels, pits, grooves, indentations, bridges, or holes to the metal substrate 22. These additional features may increase the attachment of the porous metal body to the underlying metal substrate. As depicted in FIGS. 5B and 5C, the porous metal implant 10 body can be only partially attached to the metal substrate 22 at specific structural points. Depicted as an acetabular cup 24, the cup 24 includes a ring 26 and the porous implant 10 body attaches to the ring 26 using mechanical interface 28 and metallurgical bonds. FIG. 5B depicts a C-shaped mechanical interface and FIG. 5C depicts a I-beam type mechanical interface. The percentage of the porous metal implant 10 attached using metallurgical bonds is less than about 40%. The porous metal implant 10 can also be attached to a solid core or solid body 30 as shown in FIG. 7.

The porous metal implant 10 can also be attached as part of an orthopaedic insert, such as those disclosed in U.S. patent application Ser. No. 11/111,123 filed Apr. 21, 2005, incorporated by reference. The porous metal implant 10 can also be used to form a geostructure, which is a three-dimensional geometric porous engineered structure that is self supporting and is constructed of rigid filaments joined together to form regular or irregular geometric shapes. The structure is described in more detail in U.S. Pat. No. 6,206,924, which is incorporated by reference.

Additional agents can be coated onto or in at least a surface of the porous metal implant 10. Agents include resorbable ceramics, resorbable polymers, antibiotics, demineralized bone matrix, blood products, platelet concentrate, allograft, xenograft, autologous and allogeneic differentiated cells or stem cells, nutrients, peptides and/or proteins, vitamins, growth factors, and mixtures thereof, which would facilitate ingrowth of new tissue into the porous metal implant 10. For example, if the additional agent is a peptide, an RGB peptide can be advantageously incorporated into the implant.

The description of the teachings is merely exemplary in nature and, thus, variations that do not depart from the gist of the teachings are intended to be within the scope of the teachings. Such variations are not to be regarded as a departure from the spirit and scope of the teachings.

What is claimed is:

1. A moldable mixture for making a porous metal implant, comprising:
    a. a biocompatible metal powder;
    b. a spacing agent having a sublimation or decomposition temperature; and
    c. a volatile non-polar liquid binder having a boiling point;
    wherein the spacing agent is substantially insoluble in the non-polar liquid binder, and
    wherein the difference between the sublimation or decomposition temperature of the spacing agent and the boiling point of the binder is less than 200° C.

2. The moldable mixture of claim 1 for making a porous metal implant, wherein the difference between the temperatures is less than about 100° C.

3. The moldable mixture of claim 2, wherein the difference between the sublimation or decomposition temperature of the spacing agent and the boiling point of the binder is such that the spacing agent and the binder may be removed from the mixture in a single heating.

4. The moldable mixture of claim 1, wherein the binder and the spacing agent are cohesive.

5. The moldable mixture of claim 1, wherein the biocompatible metal powder is selected from the group consisting of titanium, titanium alloys, cobalt, cobalt alloys, chromium, chromium alloys, tantalum, tantalum alloys, and stainless steel.

6. The moldable mixture of claim 5, wherein the biocompatible metal powder comprises titanium.

7. The moldable mixture of claim 1, wherein the spacing agent comprises ammonium bicarbonate.

8. The moldable mixture of claim 1, wherein the binder comprises d-limonene.

9. The moldable mixture of claim 7, wherein the binder comprises d-limonene.

10. The moldable mixture of claim 1, wherein the weight ratio of metal powder to spacing agent is from about 1:1 to about 10:1.

11. The moldable mixture of claim 1, wherein the weight ratio of the (i) binder to (ii) solid spacing agent and metal powder is from about 1:10 to about 1:30.

12. The moldable mixture of claim 1, which has been formed by application of pressure.

* * * * *